(12) United States Patent
Hjelstuen et al.

(10) Patent No.: US 9,694,092 B2
(45) Date of Patent: Jul. 4, 2017

(54) STABALISED $^{99m}$TC COMPOSITIONS

(75) Inventors: Ole Kristian Hjelstuen, Olso (NO); Grethe Karin Martinussen, Olso (NO); Gry Stensrud, Olso (NO)

(73) Assignee: GE Healthcare Limited (GB)

( * ) Notice: Subject to any disclaimer, the term of this patent is extended or adjusted under 35 U.S.C. 154(b) by 1848 days.

(21) Appl. No.: 11/721,064

(22) PCT Filed: Oct. 14, 2005

(86) PCT No.: PCT/GB2005/003975
§ 371 (c)(1),
(2), (4) Date: Sep. 1, 2009

(87) PCT Pub. No.: WO2006/064175
PCT Pub. Date: Jun. 22, 2006

(65) Prior Publication Data
US 2009/0311178 A1  Dec. 17, 2009
US 2011/0008252 A9  Jan. 13, 2011

(30) Foreign Application Priority Data

Dec. 15, 2004  (GB) .................................. 0427392.6

(51) Int. Cl.
 *A61K 51/00* (2006.01)
 *A61M 36/14* (2006.01)
 *A61K 51/04* (2006.01)

(52) U.S. Cl.
 CPC ................................ *A61K 51/0497* (2013.01)

(58) Field of Classification Search
 CPC ..... A61K 51/00; A61K 51/04; A61K 51/0497

USPC .......... 424/1.11, 1.49, 1.65, 1.69, 9.1, 1.77;
 534/7, 10–16; 206/223, 569, 570
 See application file for complete search history.

(56) References Cited

U.S. PATENT DOCUMENTS

| 4,439,413 A | 3/1984 | Hayashi et al. |
| 4,489,053 A | 12/1984 | Azuma et al. |
| 5,045,302 A | 9/1991 | Kelly et al. |

(Continued)

FOREIGN PATENT DOCUMENTS

| CN | 1331081 | * | 1/2002 |
| EP | 0483704 | | 5/1992 |

(Continued)

OTHER PUBLICATIONS

Tanno, K., Medicine and Drug Journal, 1994, vol. 30, p. 268-273.
(Continued)

*Primary Examiner* — D L Jones
(74) *Attorney, Agent, or Firm* — Wood IP LLC

(57) ABSTRACT

The present invention relates to stabilised $^{99m}$Tc radiopharmaceutical compositions of the ligand tetrofosmin, which include an ascorbic acid or ascorbate radioprotectant, in the absence of an antimicrobial preservative. The invention also provides lyophilised kits suitable for the bulk preparation of multiple unit patient doses of $^{99m}$Tc-tetrofosmin metal complexes. Also disclosed are unit doses of $^{99m}$Tc-tetrofosmin, together with processes for preparing such unit doses from the lyophilised bulk vial.

14 Claims, 2 Drawing Sheets

$^{99m}$Tc-tetrofosmin RCP (%) versus time (h) post-reconstitution.

(56) References Cited

U.S. PATENT DOCUMENTS

| | | | |
|---|---|---|---|
| 5,300,280 A * | 4/1994 | DeRosch et al. | 424/1.53 |
| 6,428,768 B1 | 8/2002 | DeRosch et al. | |
| 6,713,042 B2 * | 3/2004 | Liu | 424/1.65 |
| 7,029,653 B1 | 4/2006 | Kawai et al. | |
| 7,052,672 B2 * | 5/2006 | Forster et al. | 424/1.65 |
| 2004/0057899 A1 | 3/2004 | Forster et al. | |

FOREIGN PATENT DOCUMENTS

| | | |
|---|---|---|
| GB | 1541070 | 2/1979 |
| WO | 02/053192 | 7/2002 |

OTHER PUBLICATIONS

PCT/GB2005/003975 Int'l Search Report & Written Opinion dated Jan. 2006.
GB0427392.6 Search Report dated Mar. 2005.
PCT/GB2005/003975 Int'l Preliminary Report on Patentability Dec. 2006.
Penglis & Tsopelas "99Tcm-tetrofosmin: evaluation of fractioned cold kits." Nucl Med. Commun: vol. 21, pp. 469-472 (2000).
Metaye, et.al., "Rapid quality control for testing the radiochemical purity of 99Tcm tetrofosmin" Nucl Med Commun: vol. 22, pp. 1139-1144 (2001).
Norwegian Search Report issued May 4, 2016 in corresponding NO Appl. 20073158 filed Apr. 7, 2007.
Norwegian Office Action issued on May 4, 2016 in corresponding NO Appl. 20073158 filed Apr. 7, 2007.

* cited by examiner

Figure 1: $^{99m}$Tc-tetrofosmin RCP (%) versus time (h) post-reconstitution.
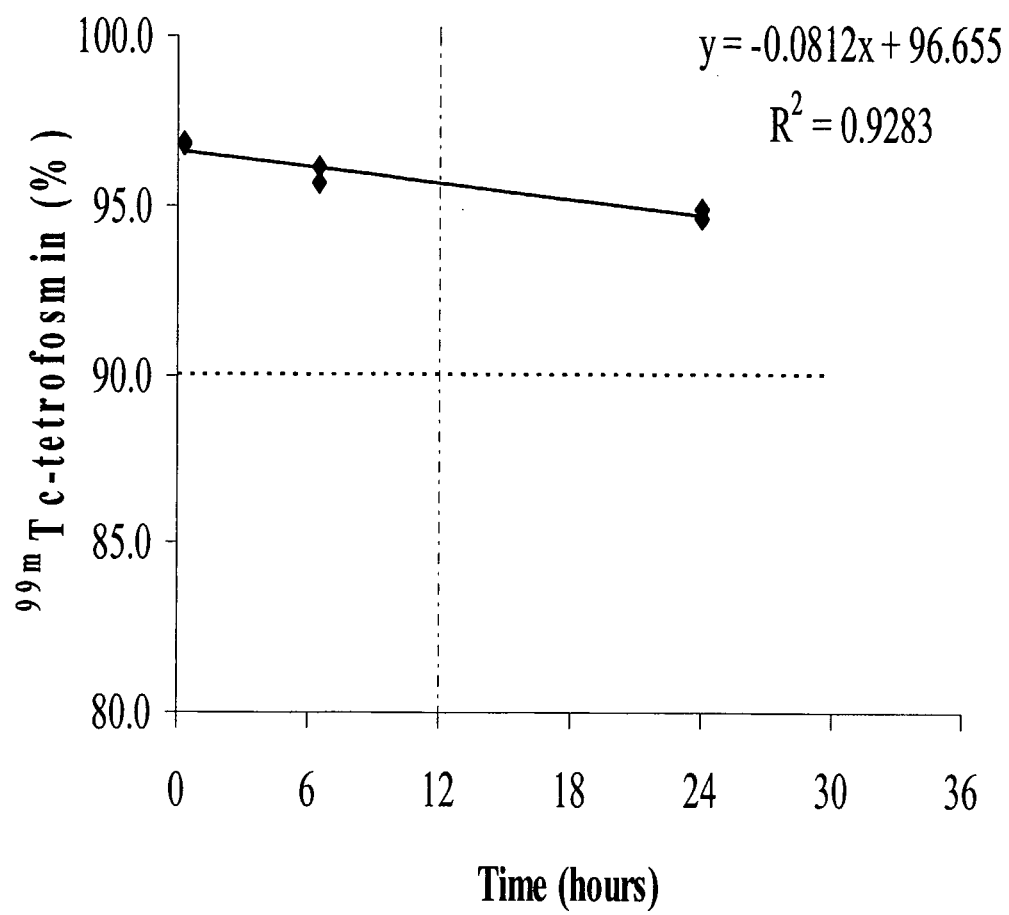

Figure 2: Slopes of $^{99m}$Tc-tetrofosmin/time (%/hour) versus RAC (GBq/ml) for Myoview™ and Myoview30.
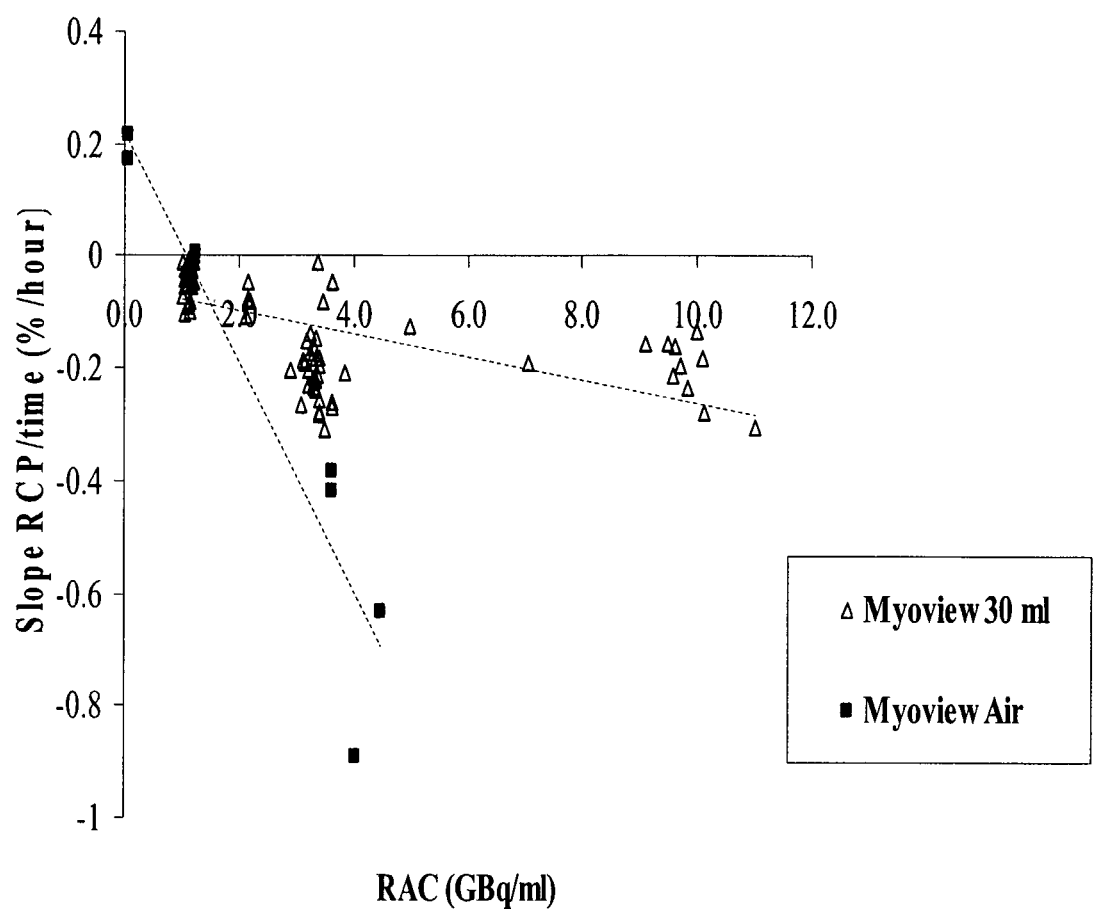

STABALISED $^{99m}$TC COMPOSITIONS

This application is a filing under 35 U.S.C. 371 of international application number PCT/GB2005/003975, filed Oct. 14, 2005, which claims priority to application Ser. No. 0427392.6 filed Dec. 15, 2004, in Great Britain the entire disclosure of which is hereby incorporated by reference.

FIELD OF THE INVENTION

The present invention relates to stabilised $^{99m}$Tc radiopharmaceutical compositions of $^{99m}$Tc-tetrofosmin, which include an ascorbic acid or ascorbate radioprotectant, in the absence of an antimicrobial preservative. Lyophilised kits suitable for the bulk preparation of multiple unit patient doses of the $^{99m}$Tc-tetrofosmin radiopharmaceutical composition are also disclosed, together with processes for preparing such unit doses from the lyophilised bulk vial.

BACKGROUND TO THE INVENTION

Diagnostic imaging radiopharmaceuticals based on the radioisotope technetium-99m ($^{99m}$Tc) are known for a variety of clinical diagnoses, including functional studies (eg. renal), and perfusion (especially heart and brain). The radioisotope $^{99m}$Tc has a half-life of 6 hours, hence such $^{99m}$Tc radiopharmaceuticals are usually prepared from so-called "kits".

These kits for the preparation of $^{99m}$Tc radiopharmaceuticals permit the user to maintain stocks of non-radioactive, lyophilised vials containing the necessary reactants, which are designed to be reconstituted with $^{99m}$Tc-pertechnetate (TcO$_4^-$) from a supply of $^{99m}$Tc to give the desired sterile $^{99m}$Tc radiopharmaceutical in a facile manner. A sterile solution of $^{99m}$Tc-pertechnetate in isotonic saline is obtained by elution of a technetium generator with sterile saline as is known in the art.

Kits for the preparation of $^{99m}$Tc radiopharmaceuticals typically contain:
 (i) a ligand which forms a metal complex with $^{99m}$Tc,
 (ii) a biocompatible reducing agent capable of reducing pertechnetate, ie. Tc(VII) to the lower oxidation state of the desired $^{99m}$Tc metal complex product.

The biocompatible reducing agent for the $^{99m}$Tc pertechnetate is typically stannous ion, ie. Sn(II). The kit may contain additional excipients, such as weak chelating agents (such as gluconate, glucoheptonate, tartrate, phosphonate or EDTA); stabilisers; pH-adjusting agents; buffers; solubilisers or bulking agents (such as mannitol, inositol or sodium chloride), to facilitate handling and lyophilisation of the kit components. To facilitate storage and distribution, the non-radioactive kits are usually supplied freeze-dried in a sterile vial with closure. The lyophilised formulation also permits facile reconstitution by the end users with sterile $^{99m}$Tc-pertechnetate in saline, to give the desired sterile, injectable $^{99m}$Tc radiopharmaceutical for human use. The shelf life of the non-radioactive technetium kit may be several months.

Radiopharmaceutical compositions may suffer from radiolysis, particularly of the solvent (typically water), with consequent generation of highly reactive free radicals, which may degrade one or more components of the kit composition post-reconstitution. It is known to employ radioprotectants or free radical scavengers to help suppress such degradation. Typically, free radical scavengers are taken from known classes of antioxidant compounds. Ascorbic acid and ascorbates are disclosed to function as stabilisers for stannous-containing non-radioactive kits for the preparation of $^{99m}$Tc radiopharmaceuticals in U.S. Pat. No. 4,364,920, and have subsequently been widely used in $^{99m}$Tc radiopharmaceutical preparations. Gentisic acid stabilisers for $^{99m}$Tc radiopharmaceuticals are disclosed in U.S. Pat. No. 4,233,284. Para-aminobenzoic acid (PABA) and related stabilisers for $^{99m}$Tc radiopharmaceutical preparations are disclosed in U.S. Pat. No. 4,451,451.

The Myoview™ kit is a 10 ml vial containing the lyophilised formulation:

| | |
|---|---:|
| Tetrofosmin | 0.23 mg |
| Stannous chloride dihydrate | 30 μg |
| Disodium sulfosalicylate | 0.32 mg |
| Sodium-D-gluconate | 1.0 mg |
| Sodium hydrogen carbonate | 1.8 mg |
| pH on reconstitution | 8.3-9.1, | which is sealed under nitrogen gas USP/NF in a 10 ml glass vial, which upon reconstitution with Sterile Sodium ($^{99m}$Tc) Pertechnetate Injection USP/Ph.Eur., yields a solution containing the heart imaging radiopharmaceutical $^{99m}$Tc-tetrofosmin. Thus, the Myoview™ kit does not contain a radioprotectant.

A ready-to-inject or "conjugate" presentation of Myoview™ has been on sale in Japan since 1997. This "conjugate" form comprises the pre-formed $^{99m}$Tc-tetrofosmin technetium complex in an aqueous solution in a syringe-vial, ie. a vial with separate plunger and needle, which is designed to be readily assembled to give a syringe containing the radiopharmaceutical. The Myoview™ "conjugate" solution contains ascorbic acid at a concentration of 1.36 mg/ml (7.7 mmolar).

Bastien et al [Nucl. Med. Comm., 20, 480-Abstract 84 (1999)] report that the order of addition of saline and pertechnetate to the Myoview™ kit can influence the radiochemical purity (RCP) of $^{99m}$Tc-tetrofosmin. Murray et al [Nucl. Med. Comm., 21, 845-849 (2000)] report that the presence of too much nitrogen gas in the headspace of the Myoview™ vial during reconstitution can lead to variable RCP results due to undesirable radiochemical impurities. Murray et al and the Package Instructions of the Myoview™ kit advocate that air is deliberately drawn into the vial during reconstitution to obviate these problems. This is achieved by withdrawing 2 ml of the headspace gas when a vent needle is in place, so that 2 ml of air is drawn into the vial. It is believed that the cause of the problem is reductive autoradiolysis, and that the introduction of oxygen inhibits this degradation.

Patel et al [J. Nucl. Med. Technol., 26(4), 269-273 (1998)] report the results of a study of commercial Myoview™ vials, and conclude that reconstitution with twice the manufacturer's upper limit of radioactivity (up to 18 GBq of $^{99m}$Tc) is successful, but do not make clear what restrictions were made on the $^{99m}$Tc-pertechnetate generator eluate used. Such greater radioactivity levels are said to confer benefits of reduced radiation exposure for personnel (one preparation instead of multiple preparations), and reduced variability in QC results. Murray et al (cited above) in fact report that use of radioactive concentrations which exceed those of the Myoview™ Package Instructions lead to poor RCP results.

WO 02/053192 discloses stabilised radiopharmaceutical compositions, which comprise:
 (i) a $^{99m}$Tc metal complex;
 (ii) a radioprotectant which comprises ascorbic acid, para-aminobenzoic acid or gentisic acid, or a salt thereof with a biocompatible cation;

(iii) one or more antimicrobial preservatives of formula (I):

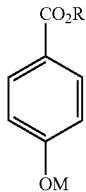

where R is $C_{1-4}$ alkyl,
and M is H or a biocompatible cation.

The Examples of WO 02/053192 include the preparation of stabilised $^{99m}$Tc-tetrofosmin complex compositions via the addition of radioprotectant and antimicrobial preservative solutions to conventional Myoview™ kits. No specific examples of lyophilised kits containing both tetrofosmin and a radioprotectant are disclosed in WO 02/053192.

THE PRESENT INVENTION

The present invention relates to kits for the preparation of stabilised $^{99m}$Tc-tetrofosmin radiopharmaceutical compositions, together with a process for the preparation of unit doses of $^{99m}$Tc-tetrofosmin.

Solving the problem of extended post-reconstitution availability of a $^{99m}$Tc radiopharmaceutical agent means that, at reconstitution, the initial level of radioactivity of $^{99m}$Tc must be high. That is because the 6 hour half-life of $^{99m}$Tc means that half the radioactivity which will be used to provide the diagnostic image is lost via radioactive decay every 6 hours, and hence only ¼ of the original radioactivity will remain after 12 hours have elapsed. Such high levels of radioactivity for extended periods pose significant potential radiolysis problems for the $^{99m}$Tc radiopharmaceutical composition.

The present invention therefore includes a radioprotectant in the composition. The $^{99m}$Tc-tetrofosmin active ingredient is susceptible to either degradation by the reducing action of the reductant (present to help effect labelling of the $^{99m}$Tc), or radiolysis. By using the stabilised compositions of the present invention, it is possible to prolong the useful lifetime post-radiolabelling, even with increased $^{99m}$Tc radioactive activity levels.

BRIEF DESCRIPTION OF THE DRAWINGS

FIG. 1 shows that the radioprotectant compositions of the present invention give satisfactory RCP of over 95% at up to 12 hours post-reconstitution (ie. the useful lifetime of the preparation).

FIG. 2 shows the results of a comparison of the rate of loss of $^{99m}$Tc-tetrofosmin RCP over time, as a function of radioactive concentration (RAC) for Myoview30 and Myoview™ (with air addition). It can be seen that the Myoview30 kit of the present invention is much more robust.

DETAILED DESCRIPTION OF THE INVENTION

In a first aspect, the present invention provides a lyophilised, non-radioactive kit which upon reconstitution with $^{99m}$Tc-pertechnetate solution gives a stabilised $^{99m}$Tc-tetrofosmin radiopharmaceutical composition, said kit having a formulation comprising:
(i) tetrofosmin;
(ii) a radioprotectant chosen from ascorbic acid or a salt thereof with a biocompatible cation;
(iii) a biocompatible reductant;
(iv) a pH-adjusting agent in an amount effective to ensure that, when the kit is reconstituted with saline the resulting solution has a pH in the range 8.0 to 9.2;
with the proviso that neither the kit nor the $^{99m}$Tc-tetrofosmin radiopharmaceutical composition contains an antimicrobial preservative.

By the term "tetrofosmin" is meant the ether-substituted diphosphine chelating agent 1,2-bis[bis(2-Ethoxyethyl)phosphino)]ethane, shown:

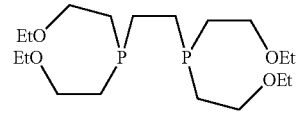

which is used in the commercial $^{99m}$Tc kit for the preparation of $^{99m}$Tc-tetrofosmin, ie. $^{99m}$Tc(O)$_2$(tetrofosmin)$_2^+$ called Myoview™.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from ascorbic acid and salts thereof with a biocompatible cation.

By the term "biocompatible cation" is meant a positively charged counterion which forms a salt with an ionised, negatively charged anionic group, where said positively charged counterion is also non-toxic at the required dosage and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium.

By the term "biocompatible reductant" is meant a reducing agent suitable for reduction of Tc(VII) pertechnetate to lower oxidation states of technetium, which is non-toxic at the required dosage and hence suitable for administration to the mammalian body, especially the human body. Suitable such reductants include: sodium dithionite, sodium bisulphite, ascorbic acid, formamidine sulphinic acid, stannous ion, Fe(II) or Cu(I). The biocompatible reductant is preferably a stannous salt such as stannous chloride or stannous tartrate.

The term "lyophilised" has the conventional meaning, ie. a freeze-dried composition, preferably one which is prepared in a sterile manner.

By the term "antimicrobial preservative" is meant an agent which inhibits the growth of potentially harmful micro-organisms such as bacteria, yeasts or moulds. An antimicrobial preservative may also exhibit some bactericidal properties, depending on the dose. Antimicrobial preservative(s) are typically used to inhibit the growth of micro-organisms in the radiopharmaceutical composition post-reconstitution, ie. in the radioactive diagnostic product itself. Antimicrobial preservatives are, however, also sometimes used to inhibit the growth of potentially harmful micro-organisms in one or more components of such non-radioactive kits prior to reconstitution. Antimicrobial preservative(s) include: the parabens, ie. methyl, ethyl, propyl or butyl paraben or mixtures thereof; benzyl alcohol; phenol; cresol; cetrimide and thiomersal. Certain such antimicrobial preservatives are too volatile to survive lyophilisation (eg. benzyl alcohol or phenol), or have very low water solubility. This makes their incorporation into a lyophilised kit designed to be reconstituted with an aqueous solvent to give a radiopharmaceutical solution problematic. Certain such antimicrobial preservatives may also form metal complexes with $^{99m}$Tc, and may therefore adversely affect the radiochemical purity (RCP) and hence the biological distribution of the $^{99m}$Tc-tetrofosmin. The presence of an antimicrobial preservative in the formulation also increases the risk of chemical incompatibility problems on kit storage, eg. due to oxygen or sulphur atom abstraction by the phosphines of tetrofosmin.

Such kits are designed to give sterile radiopharmaceutical products suitable for human administration, e.g. via direct injection into the bloodstream. The lyophilised kit is designed to be reconstituted with sterile $^{99m}$Tc-pertechnetate (TcO$_4^-$) solution from a $^{99m}$Tc radioisotope generator to give a solution suitable for human administration without further manipulation. The $^{99m}$Tc-pertechnetate solution is supplied in a biocompatible carrier. The "biocompatible carrier" is a fluid, especially a liquid, in which the radiopharmaceutical is suspended or dissolved, such that the composition is physiologically tolerable, ie. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). The biocompatible carrier may also comprise biocompatible organic solvents such as ethanol. Such organic solvents are useful to solubilise more lipophilic compounds or formulations. Preferably the biocompatible carrier is pyrogen-free water for injection, isotonic saline or an aqueous ethanol solution. As indicated above, the pH of the biocompatible carrier for intravenous injection is suitably in the range 4.0 to 10.5. The biocompatible carrier preferably comprises an aqueous solvent, and most preferably comprises isotonic saline solution. The biocompatible carrier of the present invention is employed in the absence of an antimicrobial preservative.

The kits of the present invention comprise a suitable container containing the composition of the first embodiment. The tetrofosmin may be in either free base or acid salt form, or may be a tetrofosmin non-radioactive metal complex which, upon addition of the technetium, undergoes transmetallation (i.e. metal exchange) giving the desired product. Preferably, the tetrofosmin is in free base form. Suitable containers are those which are sealed and hence permit maintenance of sterile integrity and/or radioactive safety, plus optionally an inert headspace gas (eg. nitrogen or argon), whilst also permitting addition and withdrawal of solutions by syringe. A preferred such container is a septum-sealed vial, wherein the gas-tight closure is crimped on with an overseal (typically of aluminium). Such containers have the additional advantage that the closure can withstand vacuum if desired eg. to change the headspace gas or degas solutions.

The non-radioactive kits may optionally further comprise additional components such as a transchelator, pH-adjusting agent or filler. A "transchelator" is a compound which reacts rapidly to form a weak complex with technetium, then is displaced by the ligand. This minimises the risk of formation of reduced hydrolysed technetium (RHT) due to rapid reduction of pertechnetate competing with technetium complexation. Suitable such transchelators are salts of organic acids with a biocompatible cation, especially "weak organic acids" having a pKa in the range 3 to 7. Suitable such weak organic acids are acetic acid, citric acid, tartaric acid, gluconic acid, glucoheptonic acid, benzoic acid, phenols or phosphonic. acids. Hence, suitable salts are acetates, citrates, tartrates, gluconates, glucoheptonates, benzoates, phenolates or phosphonates. Preferred such salts are tartrates, gluconates, glucoheptonates, benzoates, or phosphonates, most preferably phosphonates, most especially diphosphonates. A preferred such transchelator is a salt of gluconic acid, with a biocompatible cation, especially sodium gluconate. An additional preferred transchelator is 5-sulfosalicyclic acid or salt thereof with a biocompatible cation. Two or more transchelators may be used in combination, and the tetrofosmin kits of the present invention most preferably comprise a combination of sodium 5-sulfosalicyclate and sodium gluconate.

The term "pH-adjusting agent" means a compound or mixture of compounds useful to ensure that the pH of the reconstituted kit is within acceptable limits (approximately pH 4.0 to 10.5) for human or mammalian administration. Suitable such pH-adjusting agents include pharmaceutically acceptable buffers, such as tricine, phosphate or TRIS [ie. tris(hydroxymethyl)aminomethane], and pharmaceutically acceptable bases such as sodium carbonate, sodium bicarbonate or mixtures thereof. A preferred pH-adjusting agent for the tetrofosmin kits of the present invention is sodium bicarbonate.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose. Certain pH-adjusting agents may also function as bulking agents. A preferred such dual-function filler is sodium bicarbonate. Preferred kits of the present invention comprise a filler to facilitate lyophilisation. A preferred such filler the tetrofosmin kits of the present invention is the dual function filler sodium bicarbonate.

The incorporation of a radioprotectant in the kits of the present invention has been found to confer the advantage that the $^{99m}$Tc-tetrofosmin complex is prepared in good RCP and with good post-reconstitution stability for up to 12 hours post preparation, without the need for the air addition step taught by both the prior art and the Myoview™ Package Instructions. This is a useful simplification, since it removes a process step which means one less manipulation and hence results in reduced radiation dose for the operator, as well as being quicker and easier to carry out. The air addition step is also somewhat unusual in radiopharmacy practice and hence there is a risk that it might inadvertently be omitted, with consequent adverse effect on RCP.

The concentration of radioprotectant for use in the kits of the present invention is suitably 0.0003 to 0.7 molar, preferably 0.001 to 0.07 molar, most preferably 0.0025 to 0.01 molar. For ascorbic acid, this corresponds to a suitable concentration of 0.05 to 100 mg/cm$^3$, preferably 0.2 to 10 mg/cm$^3$, most preferably 0.4 to 1.5 mg/cm$^3$.

When the $^{99m}$Tc-tetrofosmin radiopharmaceutical of this invention is administered to a human being, a suitable amount of radioactivity to be used is in the range from 185 to 1,221 MBq (5-33 mCi). For heart imaging, when rest and stress injections are administered on the same day, the first dose should be 185-444 MBq (5-12 mCi), followed by a second dose of 555-1221 MBq (15-33 mCi) given approximately 1 to 4 hours later. Hence, the initial $^{99m}$Tc activity in the stabilised $^{99m}$Tc radiopharmaceutical compositions of the present invention is in the range 0.2 to 100 GBq, which permits multiple dosing from the same preparation even after allowing for the radioactive decay of $^{99m}$Tc.

The lyophilised kit of the present invention is preferably formulated such that the pH of the solution on reconstitution with water or saline is 8.0 to 9.2, most preferably 8.0 to 8.6. This means that, when the radioprotectant is ascorbic acid, ie. an acid, the amount of pH adjusting agent needs to be adjusted. This is necessary to ensure that the optimum pH of the kit for: $^{99m}$Tc radiolabelling of tetrofosmin; post-reconstitution stability and suitability for patient administration, are maintained. A preferred such kit formulation for a 30 ml vial presentation is given in Example 2, which shows that the amount of sodium bicarbonate has to be scaled up significantly over the conventional Myoview™ 10 ml vial formulation. The present inventors have found that, for a 30 ml vial kit, increasing the amount of ascorbic acid to 5.5 mg/vial or decreasing the amount of sodium bicarbonate to 10 mg/vial results in freeze-dried cakes with an unacceptable visual appearance. This is believed to be due to the low glass-transition temperature of ascorbic acid (−54° C.), which probably reduces the glass-transition temperature of the formulation. There is therefore an upper limit on the amount of ascorbic acid which can be added if an acceptable lyophilised kit is to be prepared. Significantly higher levels of sodium bicarbonate were found to be necessary to accommodate ascorbic acid and yet still give an acceptable lyophilised plug.

The radioprotectants of the present invention are commercially available from a number of suppliers. Tetrofosmin can be prepared as described by Chen et al [Zhong. Heyix. Zazhi, 17(1) 13-15 (1997)] or Reid et al [Synth. Appl. Isotop. Lab. Comp., Vol 7, 252-255 (2000)]. The usual synthesis involves first preparing 1,2-bis(phosphino)ethane or $H_2PCH_2CH_2PH_2$, followed by free radical addition of excess ethyl vinyl ether using a free radical initiator as described in Example 1.

In a second aspect, the present invention provides a multi-dose kit which comprises the lyophilised formulation of the first embodiment, in a sealed, sterile container fitted with a closure which permits addition and withdrawal of solutions whilst maintaining sterile integrity; wherein the kit is formulated such that 4 to 30 unit patient doses of $^{99m}$Tc-tetrofosmin radiopharmaceutical can be obtained from a single kit.

The multi-dose kit has to be sufficiently robust to withstand significantly higher levels of radioactivity, and also greater volumes of solution than the conventional Myoview™ kit. Containers for the multi-dose vial are suitably of 20 to 50 cm$^3$ volume, preferably 20 to 40 cm$^3$, most preferably 30 cm$^3$ volume. The container is fitted with a gas-tight seal which is suitable for multiple puncturing with a hypodermic needle (e.g. a crimped-on septum seal closure).

The multi-dose kit comprises sufficient material for multiple patient doses (eg. up to 100 GBq of $^{99m}$Tc per vial), whereby unit patient doses can thus be withdrawn into clinical grade syringes at various time intervals during the viable lifetime of the stabilised preparation to suit the clinical situation. The unit dose of $^{99m}$Tc-tetrofosmin radiopharmaceutical may alternatively be provided in a sealed container as described above. The term "unit patient dose" or "unit dose" means a $^{99m}$Tc-tetrofosmin radiopharmaceutical composition having a $^{99m}$Tc radioactive content suitable for in vivo imaging after administration to a single patient. Such "unit doses" are described further in the fifth embodiment (below). The multi-dose kits of the present invention are formulated to be suitable for obtaining 4 to 30, preferably 6 to 24 such unit doses of $^{99m}$Tc-tetrofosmin radiopharmaceutical in a reproducible manner for a range of $^{99m}$Tc generator eluates. It will, however, be possible to use the multi-dose kit to give 1 to 40, and perhaps even more than 40 such unit doses.

As with the first embodiment, the multi-dose kit of the second embodiment needs no air addition step in the reconstitution protocol, which is an important advantage. The multi-dose kit of the present invention also permits much more rapid preparation times for multiple $^{99m}$Tc-tetrofosmin radiopharmaceutical preparations, with substantially reduced operator radiation dose. The multi-dose kit also exhibits increased shelf-life stability of at least 78-weeks, whereas the conventional Myoview™ kit has a shelf-life stability of 37 weeks. Further advantages of the multi-dose kit are described in the process of the third embodiment (below).

In a third aspect, the present invention provides a process for the preparation of multiple unit patient doses of the radiopharmaceutical $^{99m}$Tc-tetrofosmin, which comprises:
(i) reconstituting the multi-dose kit of the second embodiment with either a sterile solution of $^{99m}$Tc-pertechnetate or first a biocompatible carrier followed by a sterile solution of $^{99m}$Tc-pertechnetate;
(ii) optionally carrying out step (i) in the presence of an antimicrobial preservative;
(iii) allowing $^{99m}$Tc tetrofosmin complex formation to take place to give a solution comprising a bulk supply of the desired $^{99m}$Tc tetrofosmin radiopharmaceutical;
(iv) optionally checking the radiochemical purity of the bulk supply of the $^{99m}$Tc tetrofosmin complex;
(v) withdrawing a unit dose from the bulk supply of step (iii) into a suitable syringe or container;
(vi) repeating step (v) with an additional syringe or container at later times to give further unit doses.

The unit dose is as defined for the first embodiment (above), and is described more fully in the fourth embodiment (below). The biocompatible carrier and preferred embodiments thereof are as defined for the first embodiment (above). A preferred biocompatible carrier for this process is sterile saline solution.

The process is preferably carried out in the absence of an antimicrobial preservative.

The sterile solution of $^{99m}$Tc-pertechnetate is preferably obtained from a technetium generator. The radioactive content of $^{99m}$Tc-pertechnetate to be used in step (i) is suitably in the range 2 to 100 GBq, preferably to 5 to 75 GBq. The radioactive concentration of $^{99m}$Tc is preferably no more than 10 GBq/cm$^3$, most preferably no more than 2.5 GBq/cm$^3$. Once prepared, the bulk supply of the desired $^{99m}$Tc tetrofosmin radiopharmaceutical has a usable shelf-life of up to 12 hours.

$^{99m}$Tc tetrofosmin complex formation, ie. step (iii), is normally complete within 15 minutes at room temperature.

The process of the present invention has the advantages over the alternative of reconstituting multiple Myoview™ 10 ml vials that:
(a) the number of manipulations involving radioactivity ($^{99m}$Tc-pertechnetate) is significantly reduced;
(b) no air addition step is necessary;
(c) only a single QC determination per batch of unit doses should be needed as opposed to a QC determination per dose;
(d) the bulk vial is formulated in such a way that the formulation can withstand a range of $^{99m}$Tc generator eluate conditions;
(e) fewer steps are involved, so automation is more facile;
(f) fewer non-radioactive kit vials are needed, so fridge storage space is saved.

The key consequences are reduced operator processing time (ie. efficiency), and reduced operator radiation dose, which are more substantial the greater the number of unit doses that are to be prepared.

In a fourth aspect, the present invention provides a stabilised radiopharmaceutical composition which comprises:
(i) the $^{99m}$Tc complex of tetrofosmin in a biocompatible carrier;
(ii) a radioprotectant at a concentration of 0.5 to 6.0 mmolar, which is chosen from ascorbic acid or a salt thereof with a biocompatible cation;
with the proviso that the radiopharmaceutical composition does not contain an antimicrobial preservative.

The "biocompatible carrier" and preferred embodiments thereof are as defined above.

A millimolar (mmolar) concentration is such that 1.0 mmolar equals 0.001 molar. The concentration of radioprotectant is preferably in the range 0.6 to 5.7 mmolar, most preferably 0.7 to 5.5 mmolar. These correspond to the concentration ranges obtained when the preferred kits of the first embodiment are reconstituted with the required volume range of $^{99m}$Tc-pertechnetate in saline. These concentrations of radioprotectant are also lower than those employed in the Myoview™ "conjugate" solution preparation which is available in Japan.

Preferred radioprotectants for the stabilised composition are as defined for the first embodiment.

Preferably the pH of the stabilised composition is in the range 7.5 to 9.0, most preferably 8.0 to 8.6.

In a fifth aspect, the present invention provides a unit patient dose of the radiopharmaceutical $^{99m}$Tc-tetrofosmin which comprises the composition of the fourth embodiment, having a $^{99m}$Tc radioactive content suitable for imaging a single patient.

The unit patient dose is as defined for the first embodiment, and is provided in a sterile form suitable for human administration in a suitable container or syringe. Such syringes are suitably for clinical use, and preferably disposable so that the syringe would only ever be used with an individual patient. The syringe may optionally be provided with a syringe shield to protect the operator from radiation dose. Suitable such radiopharmaceutical syringe shields are commercially available and preferably comprise either lead or tungsten, as described by Logan [J. Nucl. Med. Technol, 21(3), 167-170 (1993)].

The unit dose of $^{99m}$Tc-tetrofosmin radiopharmaceutical may alternatively be provided in a container which has a seal which is suitable for multiple puncturing with a hypodermic needle (e.g. a crimped-on septum seal closure). The unit dose of the present invention is preferably supplied in a clinical grade syringe, and is most preferably fitted with a syringe shield.

The $^{99m}$Tc radioactive content of the unit dose is suitably 150 to 1500 MBq, preferably 185 to 1250 MBq. When rest and stress injections are administered on the same day, the first dose should be 185 to 450 MBq, followed 1 to 4 hours later with a second dose of 550 to 1250 MBq. The preferred compositions employed in the unit dose are as described in the third embodiment (above).

The invention is illustrated by the non-limiting Examples detailed below.

Example 1 provides the synthesis of tetrofosmin. Example 2 provides a lyophilised multi-dose or "bulk" kit of the present invention, with a preferred presentation called Myoview30. Example 3 shows how a lyophilised multi-dose or "bulk" kit of the present invention can be used to prepare multiple unit doses of $^{99m}$Tc-tetrofosmin. Example 4 shows that radioprotectant-containing lyophilised kits exhibit excellent radiochemical purity over many hours post-reconstitution with $^{99m}$Tc-pertechnetate.

Example 5 shows that, even without an air addition step for the Myoview30 kit, the post-reconstitution stability of the Myoview30 kit is superior at increasing radioactive concentrations (RACs) than Myoview™. Example 5 also shows that the Myoview30 kit can be used successfully with a wider range of elution intervals for the $^{99m}$Tc generator. The range of both radioactive concentrations (RAC) and $^{99m}$Tc generator elution interval means that the kits of the present invention possess useful flexibility, especially for a radiopharmacy operation where multiple $^{99m}$Tc-tetrofosmin preparations may need to be prepared on a daily basis.

Example 6 shows that the Myoview30 kit of the present invention permits much more rapid preparation times for multiple $^{99m}$Tc-tetrofosmin radiopharmaceutical preparations, with substantially reduced operator radiation dose. The amount of radioactivity used for the QC sample is the same for Myoview30 and Myoview™, but Myoview30 involves 70% less time and 75% less radioactivity. In addition, it is easier for the operator to place 4 QC chromatography strips behind a radiation shield than 16.

Example 7 shows that a multi-dose vial of the present invention can be used to prepare 30 unit doses of $^{99m}$Tc-tetrofosmin, whilst maintaining satisfactory RCP and without compromising the sterility of the vial contents. Thus, at 12 hours post-reconstitution the RCP met the specification even after multiple stopper penetrations. No growth appeared in the culture media after 12 hours and the product complied with the USP/Ph.Eur. sterility test. The preparation dilutions examined, showed bacterial endotoxins content less than 313 IU/vial. This means that no viable bacteria or degradation products thereof were detected, and that hence the multi-dose vial functions effectively without the need for an antimicrobial preservative.

Example 8 shows that the closures of the multi-dose vials of the present invention withstand needle puncturing up to 35 times. Example 9 shows that multi-dose vials of the present invention have a usable non-radioactive shelf-life of 78-weeks (18 months) when stored at 5° C. (2° C. to 8° C.) and protected from light.

FIG. 1 shows that the radioprotectant compositions of the present invention give satisfactory RCP of over 95% at up to 12 hours post-reconstitution (ie. the useful lifetime of the preparation).

FIG. 2 shows the results of a comparison of the rate of loss of $^{99m}$Tc-tetrofosmin RCP over time, as a function of radioactive concentration (RAC) for Myoview30 and Myoview™ (with air addition). It can be seen that the Myoview30 kit of the present invention is much more robust.

EXAMPLE 1

Synthesis of Tetrofosmin

All reactions and manipulations were performed either in vacuo or under an oxygen-free nitrogen atmosphere. Solvents were dried, and degassed by nitrogen purge prior to use. α-Azo-isobutyronitrile (AIBN) and ethyl vinyl ether were obtained from BDH and Aldrich respectively. Bis (diphosphino)ethane was prepared according to the literature [Inorganic Synthesis, Vol 14, 10].

A Fischer pressure-bottle equipped with a Teflon™ stirring bar, was charged with ethyl vinyl ether (5 cm$^3$, 52.3 mmol), bis(diphosphino)ethane (1 cm$^3$, 10 mmol) and α-azo-isobutyronitrile (0.1 g, 0.61 mmol). The reaction mixture was then stirred and heated to 75° C. for 16 hours. After cooling back to room temperature, the viscous liquid was transferred to a 50 cm$^3$ round-bottomed flask. Removal of volatile materials was performed by heating under vacuum. The involatile material obtained was pure by NMR. Yield: 3.0 g, 80%.

$^1$H NMR (CDCl$_3$): δ 1.12 (12H, dt J=1.16 Hz, 7.15 Hz; OCH$_2$C$\underline{H}_3$) 1.51 (4H, br m; PC$_2$H$_4$P), 1.7 (8H; br t, J=7.4 Hz; PC$\underline{H}_2$CH$_2$OEt), 3.4 (8H, dt J=1.16 Hz, 7.15 Hz, OC$\underline{H}_2$CH$_3$), 3.49 (8H; br m; PCH$_2$C$\underline{H}_2$OEt) ppm. $^{31}$P NMR: δ −33.17 ppm.

Tetrofosmin was converted to Tetrofosmin sulphosalicylate by reaction with 2.3 to 2.5 molar equivalents of 5-sulfosalicyclic acid at room temperature in ethanol, followed by recrystallisation from ethanol/ether.

EXAMPLE 2

Lyophilised Bulk Vial Kit Formulation and Preparation

An optimised formulation for a 30 ml bulk vial preparation is as follows:

| | |
|---|---|
| Tetrofosmin | 0.69 mg, |
| Stannous chloride dihydrate | 90 μg, |
| Disodium sulfosalicylate | 0.96 mg, |
| Sodium-D-gluconate | 3.0 mg, |
| Ascorbic acid | 5.0 mg, |
| Sodium hydrogen carbonate | 11.0 mg, |
| pH on reconstitution with saline | 8.3 to 9.1. |

This kit formulation is termed "Myoview30".

Batches of 500 ml were prepared. Thus, approximately 90% of the total volume of Water for Injection (WFI) was added to a preparation vessel. The WFI was deoxygenated by purging with nitrogen. Tetrofosmin sulphosalicylate, stannous chloride dihydrate, Sodium D-gluconate, ascorbic acid and sodium hydrogen carbonate were dispensed, added and dissolved in consecutive order with constant mixing. The dispensing beakers were rinsed with deoxygenated WFI. The bulk solution was adjusted to 100% of the final volume with deoxygenated WFI during continuous mixing. The nitrogen purging was discontinued. A nitrogen blanket in headspace was applied during the rest of the manufacturing process.

The solution was sterile-filtered and 3.0 ml of the filtered solution was dispensed into 30 ml vials. The vials were partially stoppered and then lyophilised.

EXAMPLE 3

Procedure for the Reconstitution of a Bulk Radioprotectant-Containing Kit

A Myoview30 kit 30 ml vial (from Example 2) was inserted into a suitable radioactive shielding container, and the rubber septum sanitised with an isopropyl alcohol swab. A sterile needle (the venting needle) was inserted through the rubber septum. $^{99m}$Tc-pertechnetate generator eluate [10-30 cm$^3$ volume; diluted with Sodium Chloride Injection, USP as appropriate which does not contain a bacteriostat; at a radioactive concentration of up to 10 GBq/cm$^3$ and a total $^{99m}$Tc radioactive content of up to 100 GBq (2.7 Ci)] was added using a shielded, sterile syringe. The venting needle was then removed. The reconstituted vial was mixed gently for 10 seconds to ensure complete dissolution of the lyophilised powder and then incubated at room temperature for 15 minutes.

The reconstituted Myoview30 was stored at 2-25° C., and the contents used within 12 hours of preparation. Withdrawn aliquots were also stored at 2-25° C., and were used within the same 12 hour period as the reconstituted Myoview30 vial.

EXAMPLE 4

Radiochemical Analysis of Radioprotectant-Containing Lyophilised Kit RCP Over Time The radiochemical purity [RCP] of the reconstituted Myoview30 kit (Example 2) was measured using two chromatographic systems:

| | | |
|---|---|---|
| System 1: | Stationary phase: | ITLC-SG |
| | Mobile phase: | Acetone/dichloromethane [35:65 v/v] |

This system effects separation of the lipophilic $^{99m}$Tc-tetrofosmin from the $^{99m}$Tc-hydrophilics, and from the lipophilic impurities [Species B, C and X] and $^{99m}$Tc-pertechnetate.

| | | |
|---|---|---|
| System 2: | Stationary phase: | Whatman no.1 paper |
| | Mobile phase: | Acetonitrile/water [50:50 v/v] |

This system effects separation of reduced hydrolysed technetium [RHT], which remains at the origin of the strip, from the other technetium complexes that migrate.

The Myoview30 vial was reconstituted without the use of an air addition step. Results for reconstitution of a Myoview30 vial with $^{99m}$Tc-pertechnetate (37.9 GBq in 17.5 ml; RAC=2.2 GBq/ml) are given in FIG. 1.

EXAMPLE 5

Radiochemical Analysis of Radioprotectant-Containing Lyophilised Kit RCP Over Time vs the Prior Art Myoview™ kits were obtained from Amersham plc (now part of GE Healthcare). The post-reconstitution stability of the Myoview30 kit formulation of the present invention and the commercial Myoview™ 10 ml kit formulation to increasing radioactive concentration (RAC) was compared. The reconstitution procedure according to the package insert was followed for Myoview™, ie. the air addition step was followed.

The study was based on 8 preparations of Myoview™ and 89 preparations of Myoview30. Myoview™ vials were reconstituted with up to 4.5 GBq/ml, and Myoview30 vials with up to 11.0 GBq/ml. For all the 8 preparations Myoview™ was reconstituted with eluate from a $^{99m}$Tc generator eluted within a 24 hour elution interval. The Myoview30 vials were reconstituted with eluate from $^{99m}$Tc generators with various elution intervals, up to 96 hours without the use of an air addition step. The results are given in FIG. 2.

EXAMPLE 6

Comparison of Preparation Time and Operator Radiation Dose for Myoview30 vs Myoview™

16 unit doses each of 18.5 GBq (500 mCi) of $^{99m}$Tc-tetrofosmin were prepared by either:
Method 1: reconstituting 4 Myoview30 vials (from Example 2) each with 74 GBq of $^{99m}$Tc-pertechnetate;
Method 2: reconstituting 16 Myoview™ vials each with 18.5 GBq of $^{99m}$Tc-pertechnetate.
The results are given in Table 1:

| Method | Relative radiation dose to operator hands | Compounding Time (min) | QC time (min) | Total Preparation Time (min) |
|---|---|---|---|---|
| 1 | 88 | 11 | 2 | 13 |
| 2 | 175 | 28 | 7 | 35 |

EXAMPLE 7

Demonstration of Sterility of a Multi-Dose Vial

Three separate batches of Myoview30, prepared as described in Example 2, were studied. Immediately prior to the reconstitution, in each of the two vials from the three Myoview 30 ml batches, a ventilation needle, BD Microlance 21G assembled with a 0.22 μm sterile and pyrogen-free Millex GP filter, was inserted. The vials were reconstituted with 23 ml Sterile Saline Solution. Diluted $^{99m}$Tc-eluate (2 ml) was injected immediately afterwards into the vials, such that the radioactive content was ca. 2 GBq/vial. The vials were stored at 25° C. for 12 hours. After 15 minutes the vials were treated as shown in Table 2:

TABLE 2

| Time post-reconstitution, (hours) | Simulated dose volume withdrawn (mL) | Total number of individual doses withdrawn |
|---|---|---|
| 0.25 | 0.25 | 10 |
| 6 | 0.5 | 10 |
| 12 | 1 | 10 |

Thus, 30 simulated doses were withdrawn at 15 minutes, 6 hours and at the end of shelf life, 12 hours. The doses were withdrawn using 1 ml BD (Becton Dickinson) syringes assembled with BD Microlance 25 G needles. A new syringe/needle was used for each withdrawal. Doses number 1 and 21 were sent for RCP analyses. The last 'dose' (number 30) was sent for LAL (bacterial endotoxins by Limulus Amebocyte Lysate) test and test of osmotic pressure. The remaining volume in the Myoview30 vials after 12 hours, approximately 7.5 ml, was tested for sterility according to current USP/Ph.Eur Test. Thus, the remaining volume was divided in two, and sterility tests were performed and incubated in Thioglycollate Medium (TGY) and Tryptic Soy Broth (TSB) for 14 days in 25° C. and 32° C. Incubators.

LAL Test

The dose number 30 from each vial was sent for bacterial endotoxin testing. The content in the vials were initially reconstituted with 25 ml Sterile Saline Solution. Further dilution was made by taking 0.1 ml of this solution and adding to 9.9 ml Water For Injection (WFI). The LAL test was performed using the tube method. The Bacterial Endotoxin limit with this dilution was: 313 IU/vial.

Results

Sterility: The result was reported that if no growth appears in the culture media the product complies with the test for sterility (passes=P).

RCP: All preparations showed an RCP of $^{99m}$Tc-tetrofosmin of 96-97% pH: The pH of each vial was measured to be 8.2.

LAL: The result from each vial was reported that the product complies with the limit given, passes (P).

The results are summarised in Table 3:

TABLE 3

Summary results of sterility and RCP stability

| Batch | GBq/vial | Time p.r, hours | Sterility | LAL/vial |
|---|---|---|---|---|
| 1 | 2.05 | 0.25 | NA | NA |
|  | 2.04 |  |  |  |
|  | NA | 12 | P | P |
|  |  |  | P | P |
| 2 | 1.95 | 0.25 | NA | NA |
|  | 1.83 |  |  |  |
|  | NA | 12 | P | P |
|  |  |  | P | P |
| 3 | 1.97 | 0.25 | NA | NA |
|  | 2.06 |  |  |  |
|  | NA | 12 | P | P |
|  |  |  | P | P |
| Overall average | NA | NA | P | NA |

NA = not performed; P = passes.

EXAMPLE 8

Demonstration of Closure Integrity of a Multi-Dose Vial

The Myoview30 closure used was PH 701/45 red brown (1178) and the container is 30 ml vial type 1, Schott. Ten Myoview30 vials were tested according to Ph.Eur.3.2.9, except that 35 piercings were carried out compared with 10 in Ph.Eur. This was necessary to simulate the extended number of multiple dosages of a multi-dose vial. Each closure was pierced 35 times with a new hypodermic needle with an external diameter of 0.8 mm. Each piercing was on different sites. The last piercing was also an injection of ultra filtered water to nominal volume, that is 30 ml. The 10 pierced and filled vials were submerged upright in a beaker with methylene blue solution (1 g/l). The external pressure was reduced with 270 mbar to 750 mbar for 10 min.

Subsequently the atmospheric pressure was restored and the vials were left for another 30 minutes immersed in the methylene blue solution. The vials were thoroughly rinsed and inspected for any discoloration against a white background. The result of the testing showed no intrusion of dye into any of the vials.

EXAMPLE 9

Stability Testing of Multi-Dose Vials

Multiple vials from three separate batches of Myoview30, prepared as in Example 2, were stored at a controlled temperature of 5° C. protected from light. Vials were tested at intervals for up to 52 weeks storage. Tetrofosmin, ascorbic acid, stannous, disodium sulphosalicylate, oxygen content and moisture content were assayed. The purity of the tetrofosmin was monitored by $^1$H and $^{31}$P NMR. The RCP of $^{99m}$Tc-tetrofosmin prepared using the stored kits was also measured at each time point.

All results obtained showed that the product met all specifications when stored at 5° C. (2 to 8° C.) protected from light, over the full 52 week period. All the results have been evaluated and statistical analysis is performed. Linear regression analysis was carried out on quantitative parameters to investigate the relationship between each of the parameters and storage time. The correlation coefficient obtained from the regression analysis was tested for significance using Pearson's test. The 95% confidence interval for an individual parameter was calculated. When the parameter could only decrease (or increase) over time, a one sided confidence interval was calculated. The 95% confidence intervals and regression lines have been extrapolated up to 78 weeks (18 months), which is 6 months beyond the period covered by long term data. This is the maximum extension of shelf life based on the available results according to ICH (The International Conference on Harmonisation of Technical Requirements for Registration of Pharmaceuticals for Human Use) guideline Q1E. The earliest time at which the 95% confidence limit for the mean, intersects the proposed acceptance criterion is beyond the 78 weeks for samples stored at 5° C. Batches of Myoview30 stored as described above for 78 weeks, exhibited an RCP of over 90% at 12 hours post-reconstitution when reconstituted with 5.5 to 89 GBq of $^{99m}$Tc-pertechentate.

The invention claimed is:

1. A lyophilised, non-radioactive formulation in a single container, said formulation consisting of:
   (i) tetrofosmin;
   (ii) a radioprotectant selected from ascorbic acid or a salt thereof with a biocompatible cation;
   (iii) a biocompatible reductant;
   (iv) an effective amount of a pH-adjusting agent; and
   (v) at least one transchelator;
   with the proviso that an antimicrobial preservative is not present in the container and wherein the formulation having a pH in the range of 8.0 to 9.2.

2. The formulation of claim 1, wherein the at least one transchelator is selected from 5-sulfosalicylic acid and gluconic acid or salts thereof with a biocompatible cation.

3. The formulation of claim 1, wherein the biocompatible reductant comprises stannous ion.

4. The formulation of claim 1, wherein the pH-adjusting agent is sodium bicarbonate, sodium hydrogen carbonate, or a combination thereof.

5. The formulation of claim 1, wherein the container is a sealed, sterile multi-dose container fitted with a closure which permits addition and withdrawal of solutions whilst maintaining sterile integrity.

6. The multi-dose container of claim 5, wherein the container is a septum-sealed vial of 20 to 40 cm$^3$ volume.

7. A non-radioactive kit, comprising the formulation in the container of claim 1.

8. A lyophilised, non-radioactive formulation in a single container, said formulation consisting of:
   (i) tetrofosmin;
   (ii) a radioprotectant selected from ascorbic acid or a salt thereof with a biocompatible cation;
   (iii) a biocompatible reductant comprising a stannous ion;
   (iv) an effective amount of a pH-adjusting agent; and
   (v) at least one transchelator selected from 5-sulfosalicylic acid and gluconic acid or salts thereof with a biocompatible cation;
   with the proviso that an antimicrobial preservative is not present in the container and wherein the formulation having a pH in the range of 8.0 to 9.2.

9. A non-radioactive kit, comprising the formulation of claim 8.

10. The formulation of claim 8, wherein the pH-adjusting agent is sodium bicarbonate, sodium hydrogen carbonate, or a combination thereof.

11. The formulation of claim 8, wherein the container is a sealed, sterile multi-dose container fitted with a closure which permits addition and withdrawal of solutions whilst maintaining sterile integrity.

12. The multi-dose container of claim 11, wherein the container is a septum-sealed vial of 20 to 40 cm$^3$ volume.

13. A lyophilised, non-radioactive formulation in a single container, said formulation consisting of:
   (i) tetrofosmin;
   (ii) a radioprotectant selected from ascorbic acid or a salt thereof with a biocompatible cation;
   (iii) a biocompatible reductant comprising a stannous ion;
   (iv) an effective amount of sodium carbonate, sodium hydrogen carbonate, or a combination thereof as pH adjusting agent; and
   (v) at least one transchelator selected from 5-sulfosalicylic acid and gluconic acid or salts thereof with a biocompatible cation;
   with the proviso that an antimicrobial preservative is not present in the container, wherein the formulation having a pH in the range of 8.0 to 9.2,
   wherein the container is a septum-sealed, sterile multi-dose container, having a volume of 20 to 40 cm$^3$ and fitted with a closure which permits addition and withdrawal of solutions whilst maintaining sterile integrity.

14. A non-radioactive kit, comprising the formulation of claim 13.

* * * * *